(12) United States Patent
Hoagland et al.

(10) Patent No.: US 8,574,917 B2
(45) Date of Patent: Nov. 5, 2013

(54) HYDROGEN SULFIDE INDICATING PIGMENTS

(75) Inventors: William Hoagland, Boulder, CO (US); David K. Benson, Golden, CO (US); Rodney D. Smith, Golden, CO (US)

(73) Assignee: Element One, Inc., Boulder, CO (US)

( * ) Notice: Subject to any disclaimer, the term of this patent is extended or adjusted under 35 U.S.C. 154(b) by 217 days.

(21) Appl. No.: 12/324,597

(22) Filed: Nov. 26, 2008

(65) Prior Publication Data

US 2009/0137054 A1    May 28, 2009

Related U.S. Application Data

(60) Provisional application No. 61/004,244, filed on Nov. 26, 2007.

(51) Int. Cl.
*G01N 33/00* (2006.01)

(52) U.S. Cl.
USPC ........ 436/102; 436/119; 436/164; 422/82.05; 422/85

(58) Field of Classification Search
None
See application file for complete search history.

(56) References Cited

U.S. PATENT DOCUMENTS

| | | | |
|---|---|---|---|
| 3,378,348 A | | 4/1968 | McConnaughey |
| 3,563,914 A | | 2/1971 | Wattemena |
| 4,948,496 A | * | 8/1990 | Chand ........................... 204/408 |
| 5,183,763 A | | 2/1993 | Mallow et al. |
| 5,338,430 A | * | 8/1994 | Parsonage et al. ............ 204/412 |
| 5,858,307 A | | 1/1999 | Neihof |
| 6,420,181 B1 | | 7/2002 | Novak |
| 6,936,223 B2 | | 8/2005 | Lippold et al. |
| 6,939,717 B2 | | 9/2005 | Jiang et al. |
| 6,969,613 B1 | | 11/2005 | Ebiinuma et al. |
| 2004/0050143 A1 | | 3/2004 | Hoagland |
| 2004/0105980 A1 | * | 6/2004 | Sudarshan et al. ............ 428/404 |

OTHER PUBLICATIONS

Sarala et al. "High Sensitivity and selectivity of an SnO2 sensor to H2S at around 100C". Sensors and Acuators B. 1995. vol. 28, pp. 31-37.*
Gong et al. "Micromachined nanocrystalline silver doped SnO2 H2S sensor". 2005. Sensors and Actuators B. vol. 114, pp. 32-39.*
International Search Report for PCT/US08/85029, ISA/US, Mar. 24, 2009.

* cited by examiner

*Primary Examiner* — Robert Xu
(74) *Attorney, Agent, or Firm* — James R. Young; Cochran Freund & Young LLC

(57) ABSTRACT

Disclosed is a pigment that changes color upon exposure to hydrogen sulfide gas. The pigment may be ground or otherwise reduced to small particles and used in coatings, dyes, paints or inks. Potential applications for paints and inks include the production of warning indicators for the presence of hydrogen gas in areas where such presence may pose a hazard. Warning decals may be printed with pigmented ink and posted in areas of potential hydrogen hazard. In the presence of hydrogen sulfide gas, the decals can display a warning by causing a change in the color of a printed message. Objects may also be coated with pigmented paints so that if a hydrogen sulfide leak occurs from within or nearby the object, the color of the object changes to provide a warning of the presence of leaked hydrogen sulfide. Example applications of such painted objects include any industrial process containing hydrogen sulfide.

14 Claims, 4 Drawing Sheets

US 8,574,917 B2

HYDROGEN SULFIDE INDICATING PIGMENTS

CROSS-REFERENCE TO RELATED APPLICATIONS

This application claims the benefit of U.S. Provisional Application No. 61/004,244, filed Nov. 26, 2007, which is incorporated herein by reference.

BACKGROUND OF THE INVENTION

Hydrogen sulfide is a highly toxic, flammable gas that is present in many industrial process environments. Seriously toxic levels occur above 100 parts per million (ppm) in air and concentrations above 1000 ppm can be fatal. Hydrogen sulfide gas is a dense gas that can accumulate in low lying areas. Hydrogen sulfide is highly flammable and forms explosive mixtures with air over a wide range of concentrations. While hydrogen sulfide gas produces a strong odor of rotten eggs at low concentrations that readily warns of its presence, at higher concentrations or after long periods of exposure to low concentrations of this gas, the human olfactory senses are dulled and dangerously high concentrations may go undetected by the nose.

SUMMARY OF THE INVENTION

An embodiment of the present invention may therefore comprise a hydrogen sulfide gas detector comprising: a pigment that comprises a metal organic compound that is in the form of micro-size particles which directly and spontaneously react with hydrogen sulfide gas and create colored metal sulfides; a carrier that provides a medium for disposing the pigment on a surface for exposure to the hydrogen sulfide gas.

An embodiment of the present invention may further comprise a hydrogen sulfide gas detector comprising: a pigment that comprises a metal oxide powder, that is in contact with a hydrogen sulfide reactive metal, that is reduced to a suboxide by hydrogen that is produced during a reaction between the hydrogen sulfide gas and the hydrogen sulfide reactive metal; a carrier that provides a medium for disposing the pigment on a surface for exposure to the hydrogen sulfide gas.

An embodiment of the present invention may further comprise a pigment for detecting hydrogen sulfide gas comprising: a metal organic compound that is ground into micro-sized particles in the range of approximately 10 to 100 microns which directly and spontaneously react with hydrogen sulfide gas and create colored metal sulfides.

An embodiment of the present invention may further comprise a pigment for detecting hydrogen sulfide gas comprising: a metal oxide powder; a hydrogen sulfide reactive metal that is in contact with the metal oxide powder that reacts with the hydrogen sulfide gas and produces hydrogen that reacts with the metal oxide powder which causes the metal oxide powder to be reduced to a suboxide.

An embodiment of the present invention may further comprise a method of making a hydrogen sulfide detector comprising: providing a metal organic compound that directly and spontaneously reacts with hydrogen sulfide gas and creates colored metal sulfides; mixing the metal organic compound with a carrier that provides a medium for disposing the pigment on a surface for exposure to hydrogen sulfide gas.

An embodiment of the present invention may further comprise a method of making a hydrogen sulfide detector that detects hydrogen sulfide gas comprising: providing a metal oxide powder; contacting the metal oxide powder with a hydrogen sulfide reactive metal that produces hydrogen upon reaction with the hydrogen sulfide gas, which reacts with the metal oxide powder and causes the metal oxide powder to be reduced to a suboxide; mixing the metal oxide powder and the hydrogen sulfide reactive metal in a carrier.

An embodiment of the present invention may further comprise a hydrogen sulfide gas detector comprising: pigment means that comprise a metal organic compound that is in the form of micro-size particles which directly and spontaneously react with hydrogen sulfide gas and create colored metal sulfides; carrier means that provide a medium for disposing the pigment on a surface for exposure to the hydrogen sulfide gas.

An embodiment of the present invention may further comprise a hydrogen sulfide gas detector comprising: pigment means that comprise a metal oxide powder, that is in contact with a hydrogen sulfide reactive metal, that is reduced to a suboxide by hydrogen that is produced during a reaction between the hydrogen sulfide gas and the hydrogen sulfide reactive metal; carrier means that provide a medium for disposing the pigment on a surface for exposure to the hydrogen sulfide gas.

DETAILED DESCRIPTION OF THE EMBODIMENTS

Figure 1:
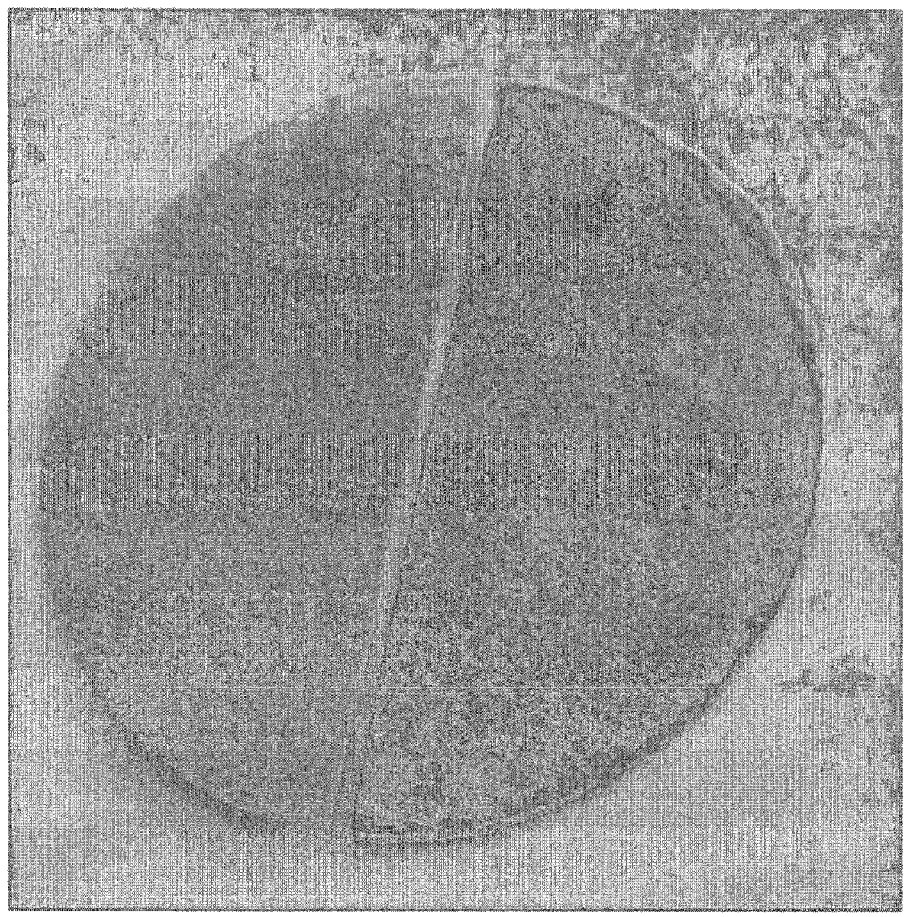
FIG. 1 shows a molybdenum trioxide/silver hydrogen sulfide gas indicator.

The various embodiments disclosed herein identify a group of pigments that change color to visually indicate the presence of hydrogen sulfide gas. Such pigments may be readily incorporated into a matrix to form a paint, an ink, a dye, a polymer composite sheet, or function as a dispersion in a porous material such as paper.

Hydrogen sulfide is produced in many commercial processes. For example, hydrogen sulfide is produced in large quantities during the processing of sulfide mineral ores, and in the recovery and processing of natural gas and petroleum. It is used in the tanning of hides and processing of paper products and numerous other chemical processes. Hydrogen sulfide commonly occurs in the airborne effluent from waste disposal processes as one product of sulfate reducing bacteria.

Because of its hazardous nature, hydrogen sulfide must be detected at very low concentrations in the workplace. In industrial processing facilities, where hydrogen sulfide is a potential hazard, electronic gas detectors are commonly used to provide a warning signal whenever the concentration of the gas exceeds an acceptably low level. These electronic gas detectors have certain limitations. Electronic detectors are relatively expensive and require regular maintenance and calibration. Electronic detectors require electrical wiring to provide power for operation and to transmit warning signals back to activation devices or warning devices. Electronic devices survey a relatively large, typically room-sized area. Since electrical detectors typically require household current, these detectors do not function during an electrical failure.

There has been a long recognized and urgent need to complement the function of electronic gas detectors for improved hydrogen sulfide safety. In particular, a visual indicator of the presence of hydrogen sulfide gas can provide a needed additional warning. Indicators can take various forms, such as warning signs, placards, or devices that just simply change colors or shades, such as disclosed in more detail below with respect to FIG. 4. Similar visual indicators for displaying the presence of hazardous hydrogen gas are more fully disclosed in U.S. Pat. No. 6,895,805, U.S. patent application Ser. No. 11/470,218, U.S. patent application Ser. No. 11/553,400, and U.S. patent application Ser. No. 11/685,179, which are specifically incorporated herein by reference for all that they disclose and teach. A low cost indicator, that is disclosed in the various embodiments herein, requires no electrical power, is inexpensive and provides a needed supplement or replacement for electronic gas detectors. The various embodiments can be used in numerous specific sites where hydrogen sulfide gas might be present that are part of a larger area that is also monitored by electronic gas detectors. Being deployed more locally and closer to a potential hydrogen sulfide source, provides an early warning of insidious hydrogen sulfide gas sources before such sources produce gas that spreads into larger areas in concentrations that are high enough to trigger electronic gas detector alarms.

The electronic detection of a hydrogen sulfide concentration above acceptable levels usually triggers a shutdown of a process line that may be the source of the gas, which in turn requires maintenance operations to locate and fix the source of the hydrogen sulfide leak. Such shutdowns can be quite expensive because of lost production, wasted labor time, and lengthy restart procedures. These costs are in addition to the costs of repairing the source of the gas. Locating the source of a hydrogen sulfide gas quickly, by having multiple detectors, will result in shorter shutdown periods and less expensive start-up procedures. If a source of hydrogen sulfide gas can be detected and repaired before it is large enough to trigger a safety alarm, costly shutdown procedures may be prevented.

Pigment color change, in accordance with the various embodiments disclosed herein, occurs by chemical reaction between hydrogen sulfide gas and the pigment material. Two different classes of materials are used as pigments:
1. Metal organic compounds that directly and spontaneously react with hydrogen sulfide to produce colored metal sulfides. These include organic compounds of lead, bismuth, copper or silver. These can comprise organic metal salts of acetic acid, citric acid and the like.
2. Metal oxides that are readily reduced to a colored suboxide by atomic hydrogen. Such metal oxides, when activated by a partial coating of a hydrogen sulfide-reactive metal such as silver or copper, are readily reduced to a colored sub-oxide by the hydrogen that is produced during the reaction of the hydrogen sulfide gas and the metal coating. The metal oxides include transition metal oxides, such as tungsten oxide, molybdenum oxide and niobium oxide. These transition oxides may be at least partially coated with a hydrogen sulfide reactive metal, such as silver, copper or the like.

In one example, lead acetate powder is ground to microsized particles, typically in the range of approximately 10-100 microns. Such particles are suitable for use as pigments for paints and inks and for dispersion in polymer sheets or in porous materials. The reaction of this powder with a low concentration of hydrogen sulfide gas results in a rapid visible change of color from white to brown.

In another example, tungsten oxide coated with a superficial layer of silver changes from a white to a blue color when exposed to a low concentration of hydrogen sulfide. The silver may be added mechanically by mixing the tungsten oxide powder with microscopic silver particles causing the silver to adhere to the tungsten oxide. The silver may also be added to the surface of the tungsten oxide particles by chemical reduction of a silver compound in contact with the tungsten oxide powder by heating the powder and silver compound in a reducing atmosphere such as forming gas (hydrogen-nitrogen gas mixture).

In addition to pigment powders, the indicators can also take the form of thin films composed of any of the above mentioned metals: lead, bismuth, copper, or silver. These metallic, thin films can be deposited by numerous techniques including thermal evaporation, magnetron sputtering, or electrochemical methods. The structure of the film is composed of small metallic islands deposited on an underlying film with low adhesion such as polytetrafluoroethylene (PTFE). The resulting films can be used for various applications such as decals, placards or telltale tags.

For example, a thin film of 6 nm metallic silver is deposited on an underlying layer of 100 nm PTFE. An additional layer of 100 nm PTFE is added over the silver as a protective coating. The resulting film changes from light yellow to a rust color after exposure to a low concentration of Hydrogen Sulfide.

The pigments of the various embodiments disclosed herein have the advantage of being easily used and easily incorporated into many carriers, such as commercially available specialty coatings, paints, inks and dyes. These products can be applied as they normally would and additionally provide for a long lifetime with high mechanical durability that resists degradation in environments containing many pollutants. In addition, the products using the hydrogen sulfide detector pigments are very inexpensive, compared to other available sensors, such as electronic sensors. The various embodiments reflect a new generation of low-cost hazardous hydrogen sulfide gas indicators. The various embodiments reduce the risk to personnel and property by continuously indicating the presence, or absence, of leaking hydrogen sulfide gas.

Another example of a pigment for detecting hydrogen sulfide is molybdenum trioxide-silver pigment. Silver nano-particles (particle size typically less than 100 nanometers in diameter, $10^{-7}$ m) are mechanically mixed with a fine powder of molybdenum trioxide (particle size typically less than 100 microns in diameter, $10^{-4}$ m) by grinding or ball-milling the two components together dry. The resulting powder consists of fine molybdenum trioxide particles with attached silver nano-particles. The proportion of silver to molybdenum oxide is typically 0.05% by weight.

When these particles are exposed to hydrogen sulfide gas, the gas reacts with the silver to produce silver sulfide and hydrogen gas. The change of silver to silver sulfide produces only an imperceptible change in coloration due to the small amount of silver and the very small silver particle size. However, the hydrogen produced in the reaction readily reduces part of the molybdenum trioxide thereby changing the color of the molybdenum trioxide from light gray to dark blue-black. The partially reduced molybdenum trioxide is stable in air.

FIG. 1 shows two halves of a circular filter paper covered with the molybdenum trioxide: silver nano-particle mixture (0.05% silver by weight). The right half has been momentarily exposed to hydrogen sulfide gas. The contrast in color is readily visible and is persistent. The left side has not been exposed.

Another example of a pigment for detecting hydrogen sulfide is tungsten trioxide-silver pigment. The pigment is made in the same way as described in the example above with regard to molybdenum trioxide-silver, except that a fine powder of tungsten trioxide is used in place of the molybdenum trioxide and a larger proportion of nano-particle silver is mechanically mixed with the oxide (typically 0.5% by weight).

When these particles are exposed to hydrogen sulfide gas, the gas reacts with the silver to produce silver sulfide and hydrogen gas. The change of silver to silver sulfide produces only an imperceptible change in coloration due to the small amount of silver and the very small silver particle size. However, the hydrogen produced in the reaction readily reduces part of the tungsten trioxide thereby changing the color of the tungsten trioxide from light gray-green to dark blue-green-black. The partially reduced tungsten trioxide is not completely stable and will re-oxidize in air over time. Thus the change in color is not as persistent as in the molybdenum trioxide example above.

Figure 2:
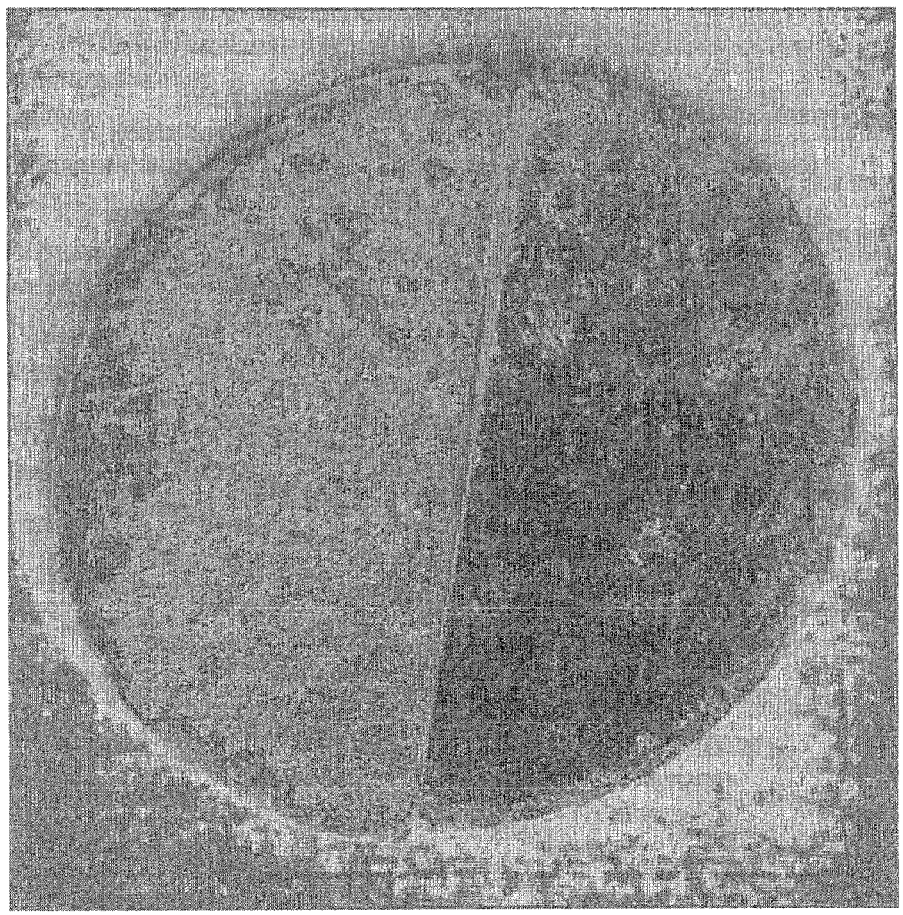
FIG. 2 shows a tungsten trioxide/silver hydrogen sulfide gas indicator.

FIG. 2 shows two halves of a circular filter paper covered with the tungsten trioxide: silver nano-particle mixture (0.5% silver by weight). The right half has been momentarily exposed to hydrogen sulfide gas. The left half has not been exposed. The contrast in color is readily visible but will fade over time. This feature allows the tungsten oxide based example to function a number of times to indicate a number of different exposures to hydrogen sulfide gas over a period of time whereas the molybdenum trioxide will persistently indicate only a single exposure.

A further example of a pigment for detecting hydrogen sulfide is a thin film molybdenum trioxide-silver indicator. Molybdenum trioxide is deposited as a one micron ($10^{-6}$ m) thick film by thermal evaporation in vacuum and then overlaid with a 0.1 nanometer ($10^{-10}$ m) thick layer of thermally evaporated silver. The silver deposit is superficial and results in nano-particle islands of silver dispersed on the surface of the continuous molybdenum trioxide underlying film.

The resulting two-layer film is transparent and nearly colorless. When the film is exposed to hydrogen sulfide gas, the gas reacts with the silver to produce silver sulfide and hydrogen gas. The change of silver to silver sulfide produces only an imperceptible change in coloration due to the small amount of silver and the very small silver particle size. However, the hydrogen produced in the reaction readily reduces part of the molybdenum trioxide thereby changing its color from light gray to blue, the darkness of which depends upon the amount of hydrogen sulfide gas to which it has been exposed.

Figure 3:
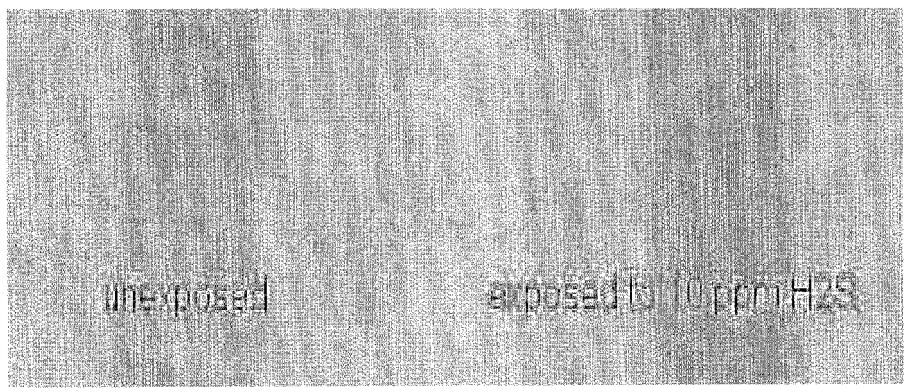
FIG. 3 shows a thin film molybdenum trioxide/silver hydrogen gas indicator.

FIG. 3 shows two examples of the thin film molybdenum trioxide-silver indicator. The film on the left is unexposed and the film on the right has been exposed to 10 parts per million (ppm) concentration of hydrogen sulfide gas in nitrogen.

Figure 4:
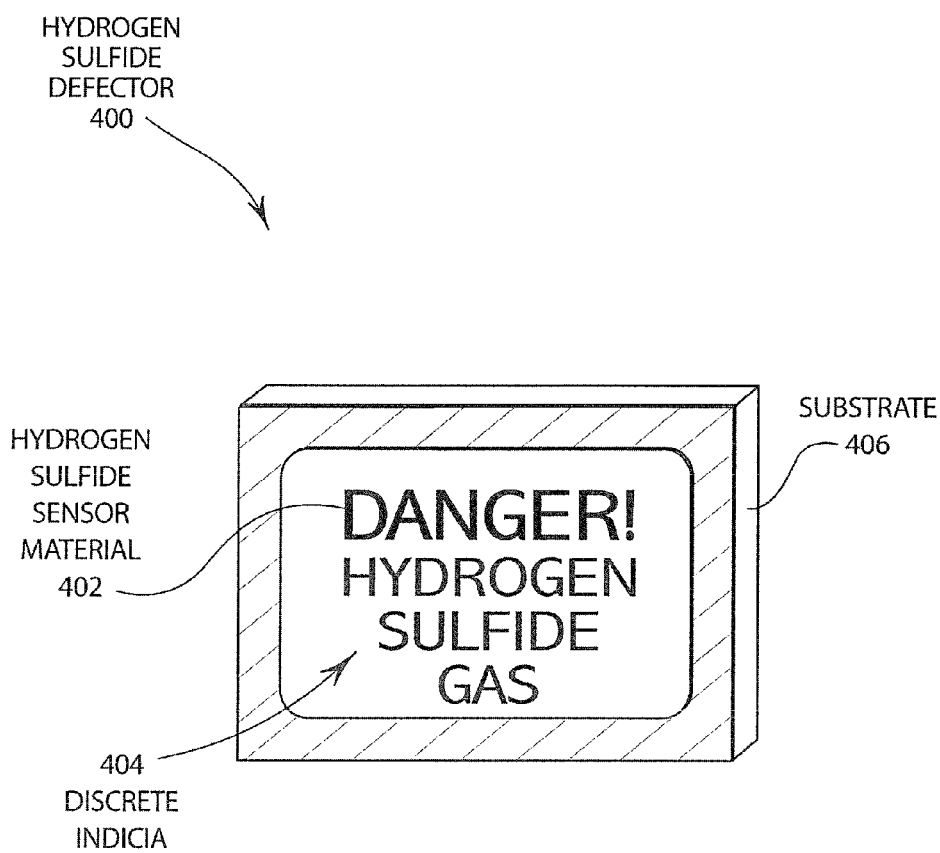
FIG. 4 is a schematic illustration of a hydrogen sulfide detector.

FIG. 4 is a schematic illustration of a hydrogen sulfide detector 400 that is in the form of a placard or sign. As shown in FIG. 4, the sign includes hydrogen sulfide sensor material 402, such as described above, that forms a set of discrete indicia 404 indicating when hydrogen sulfide gas is present. In other embodiments, the discrete indicia 404 can include alphanumeric characters or symbols arranged in any number, variety or combination of languages or notations. The alphanumeric indicia or symbols can also provide additional information. For example, the alphanumeric indicia 404 can provide a warning, instructions, a map, display, guidance or other information relevant to the detection of hydrogen sulfide gas.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A hydrogen sulfide gas detector comprising:
    a pigment comprised of metal oxide powder particles that are partially coated with islands or particles of a hydrogen sulfide reactive metal selected from a group consisting of metallic silver and metallic copper, which is reactive with hydrogen sulfide in a manner that produces hydrogen, wherein said metal oxide powder particles comprise a transition metal oxide selected from a group consisting of tungsten oxide, molybdenum oxide, and niobium oxide, which is reducible to a colored sub-oxide by hydrogen;
    a carrier that provides a medium for disposing said pigment on a surface for exposure to hydrogen sulfide gas in an environment.

2. The detector of claim 1 wherein said hydrogen sulfide reactive metal comprises silver that is partially coated on said metal oxide powder particles by chemical reduction of a silver oxide compound in contact with the metal oxide powder particles.

3. The detector of claim 1 wherein said hydrogen sulfide reactive metal comprises powdered silver that is partially coated on said metal oxide powder particles by mechanically mixing said powdered silver and said metal oxide powder particles together dry in a manner that causes the powdered silver to adhere to the metal oxide powder particles.

4. The detector of claim 1 wherein said carrier comprises paint.

5. The detector of claim 1 wherein said carrier comprises an ink.

6. The detector of claim 1 wherein said carrier comprises a dye.

7. The detector of claim 1 wherein said carrier comprises a polymer.

8. The detector of claim 1 wherein said carrier comprises a porous material.

9. A pigment for detecting hydrogen sulfide gas comprising:
    metal oxide powder particles comprising a metal oxide that is reduceable to a colored sub-oxide by hydrogen selected from a group consisting of tungsten oxide, molybdenum oxide, and niobium oxide;
    islands or particles of a hydrogen sulfide reactive metal that is superficially adhered onto the metal oxide powder particles in a manner that partially coats said metal oxide powder particles, said hydrogen sulfide reactive metal being selected from a group consisting of silver and copper, which is reactive with hydrogen sulfide in a manner that produces hydrogen.

10. The detector of claim 9 wherein said hydrogen sulfide reactive metal comprises islands of silver that is superficially adhered on said metal oxide powder by chemical reduction of a silver compound in contact with the metal oxide powder particles.

11. The detector of claim 9 wherein said hydrogen sulfide reactive metal comprises particles of silver that is superficially adhered on said metal oxide powder particles by mechanically mixing said particles of silver and said metal oxide powder particles together dry in a manner that causes the particles of silver to adhere to the metal oxide powder particles.

12. A method of making a hydrogen sulfide detector material that detects hydrogen sulfide gas comprising:
    providing a metal oxide powder comprising powder particles of a metal oxide selected from a group consisting of tungsten oxide, molybdenum oxide, and niobium oxide, which is reducible to a colored sub-oxide by hydrogen;
    partially coating said metal oxide powder particles with islands or particles of a hydrogen sulfide reactive metal selected from a group consisting of silver and copper, which produces hydrogen upon reaction with hydrogen sulfide gas;
    mixing said partially coated metal oxide powder particles with a carrier.

13. The method of claim 12 wherein said partially coating said metal oxide powder particles with said hydrogen sulfide reactive metal comprises:
    mechanically dry mixing said metal oxide powder with a silver metal powder comprising silver particles to adhere the silver particles to the metal oxide powder particles.

14. A hydrogen sulfide gas detector comprising:
    pigment means that comprise metal oxide powder particles selected from a group consisting of tungsten oxide powder particles, molybdenum oxide powder particles, and niobium oxide powder particles, which are reducible by hydrogen to colored sub-oxide particles, said metal oxide powder particles being partially coated with islands or particles of a hydrogen sulfide reactive metal selected from a group consisting of silver and copper, which produces hydrogen upon reaction with hydrogen sulfide gas; and
    carrier means that provide a medium for disposing said pigment means on a surface for exposure to hydrogen sulfide gas in an environment.

* * * * *